(12) United States Patent
van der Woude et al.

(10) Patent No.: US 6,313,104 B1
(45) Date of Patent: Nov. 6, 2001

(54) ORGANOPROTECTIVE SOLUTIONS

(75) Inventors: F. J. van der Woude, Hirschberg-Leutershausen (NL); Benito Yard, Freinsheim (DE); Dieter Herr, Altrip (DE); Volker Laux, Mainz (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/235,235

(22) Filed: Jan. 22, 1999

(51) Int. Cl.[7] ........................ A61K 31/715; A61K 31/725
(52) U.S. Cl. .................. 514/54; 514/53; 514/56; 514/60
(58) Field of Search .................. 514/53, 54, 56, 514/60

(56) References Cited

U.S. PATENT DOCUMENTS

| | | | |
|---|---|---|---|
| 4,686,288 | 8/1987 | Lormeau et al. | 536/21 |
| 4,727,063 | 2/1988 | Naggi et al. | 514/56 |
| 4,798,824 | 1/1989 | Belzer et al. | 514/60 |
| 4,873,230 | 10/1989 | Belzer et al. | 514/60 |
| 4,879,283 * | 11/1989 | Belzer et al. | 514/60 |
| 4,920,004 | 4/1990 | Bagchi | 428/407 |
| 4,948,881 | 8/1990 | Naggi et al. | 536/20 |
| 4,966,894 | 10/1990 | Herr et al. | 514/56 |
| 5,013,724 * | 5/1991 | Petitou et al. | 514/54 |
| 5,032,679 | 7/1991 | Brandley et al. | 536/21 |
| 5,104,787 * | 4/1992 | Lindstrom et al. | 435/1 |
| 5,200,398 | 4/1993 | Strasberg et al. | 514/23 |
| 5,236,910 | 8/1993 | Egidio et al. | 514/56 |

FOREIGN PATENT DOCUMENTS

| | | |
|---|---|---|
| 037319 | 10/1981 | (EP) . |
| 269937 | 6/1988 | (EP) . |
| 2538404 | 6/1984 | (FR) . |

OTHER PUBLICATIONS

Hizukuri. Carbohydrates In Food. Edited by Ann–Charlotte Eliasson. New York. Marcel Dekker, Inc. 1996. pp. 366–368.*
Yard et al., *Transplantation*, vol. 66, No. 9, pp. 1244–1250, Nov. 16, 1998.
Yard et al., *Transplantation*, 66(9), 1244–1250, 11/ 98.
van der Pijl et al., *J. Amer. Soc. Nephrol*, 8, 1997, p. 456–462.
Douglas et al., *Clin. Exp. Immun.* 107, 1997, 578–584.
Collins et al., *Lancet 2*, 1969, 1219–1222.
Sacks et al., *Lancet 1*, 1973, 1024–1028.
Siegel et al., *Am. J. Phys.*, 254, 1983, F530–F534.
Belzer et al., *Transpl. Proc.*, 16, 1984, 161–163.
Jamieson et al., *Transplantation*, 46, 1988, 517–522.
Ploeg et al., *Transplantation*, 46, 1988, 191–196.
Wicomb, *Transplanation*, 47, 1988, 733–734.
Wolfrom et al., *J. Am. Chem. Soc.*, 75, 1953, 1519.
Shively et al., *Biochemistry*, 15(18), 1976, 3932–3942.
Charles et al., *Biochem. J.*, 30, 1936, 1927–1933.
Coyne, *Chem. and Biol. of Heparin*, 1981, 9–17.
Dietrich, *Biochem. J.*, 108, 1968, 647–654.
Fuchs et al., *Lebensm. Unters. Forsch.*, 198, 1994, 486–490.

* cited by examiner

Primary Examiner—Gary Geist
Assistant Examiner—Everett White
(74) Attorney, Agent, or Firm—Keil & Weinkauf

(57) ABSTRACT

The invention relates to the use of polysulfated glycosaminoglycans having a sulfur content of at least 12.5% for producing pharmaceutical preparations for inhibiting the γ-interferon-induced upregulation of the MHC Class I and MHC Class II proteins and ICAM-1. The invention furthermore relates to organoprotective solutions comprising polysulfated glycosaminoglycans and to a process for the ex-vivo protection of transplant organs.

8 Claims, 18 Drawing Sheets

ORGANOPROTECTIVE SOLUTIONS

BACKGROUND OF THE INVENTION

The invention relates to the use of polysulfated glycosaminoglycans having a sulfur content of at least 12.5% for producing pharmaceutical preparations for inhibiting the γ-interferon-induced upregulation of the MHC Class I and MHC Class II proteins and ICAM-1. The invention furthermore relates to organoprotective solutions comprising polysulfated glycosaminoglycans and to a process for the ex-vivo protection of transplant organs.

The use of glycosaminoglycans and specifically of heparins and heparinoids for producing pharmaceutical preparations for treating perfusion disorders is well known.

The use of glycosaminoglycans for a number of other diseases has recently been described. Thus, U.S. Pat. No. 5,236,910 claims the use of glycosaminoglycans for treating diabetic nephropathy and neuropathy. The use of low molecular weight heparins for the same indication is described by van der Pijl et al. (J. Americ. Soc. Nephrol. 8 (1997), 456–462).

U.S. Pat. No. 5,032,679 claims the use of glycosaminoglycans for inhibiting the proliferation of smooth muscle cells and the diseases associated therewith.

U.S. Pat. No. 4,966,894 claims polysulfated heparins for treating diseases caused by retroviruses.

Granlinski et al. describe the modulation of the complement system by polysulfated heparins.

In Clin. Exp. Immunol. 107 (1997), 578–584, Douglas et al. study antagonization of the inflammation-promoting activity of γ-inteferon with heparin, heparan sulfate or heparin-like molecules. Heparin is capable of influencing the immunogenic effect of γ-inteferon.

In the transplantation of organs, undesirable rejections are frequently observed. A large number of different approaches have been used to prevent these rejections. Thus, first, the histo-compatibility antigens of donor and recipient are compared. Only those organs are transplanted whose donor and recipient have, if possible, identical, or very similar, histo-compatibility antigens. Inspite of this, undesirable organ rejections are frequently observed. For example, an acute renal allograft rejection is observed, whose main effect is the recognition of the allo-MHC antigens by T lymphocytes, resulting in a lysis of the tubular cells. Also observed is the "graft versus host reaction", a strong reaction of the immune cells of the donor, which are transplanted with the organ, against the recipient. Cytotoxic T cells and antibodies against the host organism are formed.

To further reduce the risk of a graft rejection, the organs are cooled immediately after harvest and stored in an organo-protective solution. Furthermore, drugs are administered to the recipient to suppress the immune response of the recipient.

A large number of organoprotective solutions are described in the literature. Thus, Collins et al. (Lancet 2 (1969), 1219) describe intracellular electrolyte solutions for preserving the organs. Sacks S. A. (Lancet 1 (1973), 1024) describes solutions having an osmotically stabilizing effect. ATP-MgCl$_2$, AMP-MgCl$_2$ and inosine are described as being advantageous agents in such solutions (Siegel, N. J. et al., Am. J. Physiol. 254 (1983), F530, Belzer et al., Transpl. Proc. 16 (1984), 161). U.S. Pat. No. 4,920,004 claims a solution containing mannitol, adenosine and ATP-MgCl$_2$. U.S. Pat. Nos. 4,798,824 and 4,873,230 claim an organo-protective solution which contains hydroxyethyl starch. U.S. Pat. No. 4,879,283 claims a solution which contains KH$_2$PO$_4$, MgSO$_4$, adenosine, allopurinol, raffinose and hydroxyethylcellulose. This solution is known as University of Wisconsin solution (=UW-solution) and is described as having been used for successful preservation of liver, kidneys and heart (Jamieson et al., Transplantation 46 (1988), 517, Ploeg et al., Transplantation 46 (1988) 191 and Wicomb, W. N., Transplantation 47 (1988), 733). In U.S. Pat. No. 5,200,398, glucoronic acid, and salts and esters thereof are described for use as a further additive in these protective solutions.

Inspite of the successes that have been achieved in the protection of organs for transplantation and in suppressing undesirable organ rejections, there is still a demand for further improvement.

BRIEF SUMMARY OF THE INVENTION

It is an object of the present invention to provide further improvements both in organoprotection prior to and during transplantation and to further reduce the risk of organ rejection.

We have found that this object is achieved by using polysulfated glycosaminoglycans having a sulfur content of at least 12.5% by weight for producing pharmaceutical preparations for inhibiting the γ-interferon-induced upregulation of the MC Class I and MHC Class II proteins and ICAM-1.

The invention furthermore relates to organoprotective solutions which comprise such an amount of a polysulfated glycosaminoglycan having a sulfur content of at least 12.5% by weight that it is effective in maintaining cell integrity and cell vitality.

DETAILED DESCRIPTION OF THE INVENTION

Figure 1:
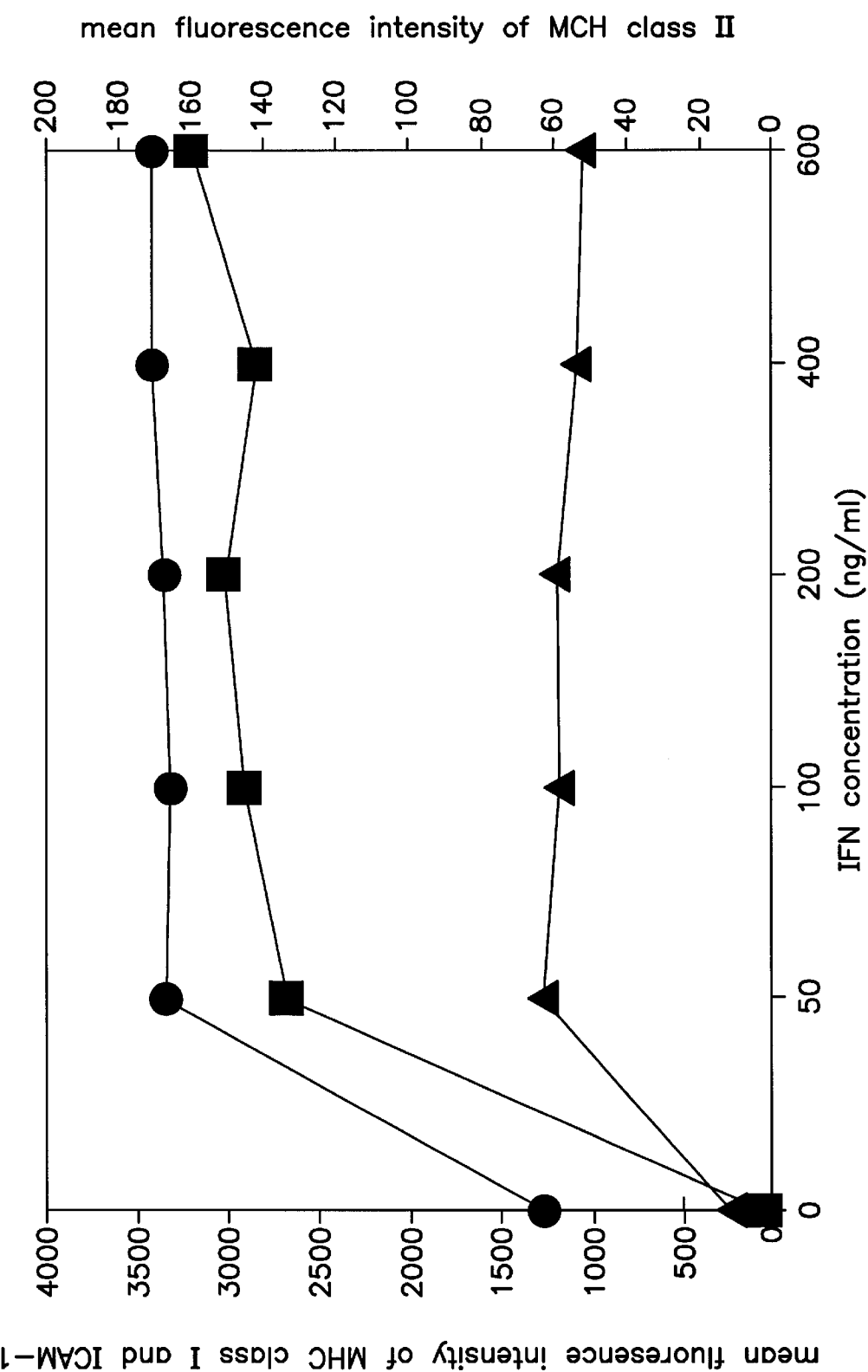
FIG. 1 shows the dose-response of IFN-γ on MHC class I, class II and ICAM-1 expression on PTEC.

The pharmaceutical preparations produced for the use according to the invention, which include, for example, the organoprotective solutions, may contain the abovementioned compounds as free compounds or in the form of their physiologically active salts or esters, their tautomers and/or isomeric forms or in the form of a combination of the free compounds and the various salts. Examples of advantageous physiologically active salts which may be mentioned are the Na, Ca or Mg salts. Salts with organic bases such as diethylamine, triethylamine or triethanolamine are also suitable. The pharmaceutical preparations may advantageously contain at least one free substance or at least one compound in the form of its salt or mixtures thereof.

The polysulfated glycosaminoglycans (=mucopolysaccharides) utilized for the use according to the invention mean negatively charged polysaccharides (=glycans) consisting of variously linked disaccharide units in which, for example, 1 molecule of a uronic acid such as D-glucuronic acid or L-iduronic acid is glycosidically linked to the 3 or 4 position of an amino sugar such as glycosamine or galactosamine. At least one of the sugars in the disaccharide has a negatively charged carboxylate or sulfate group which may be linked via an oxygen or a nitrogen atom. Glycosaminoglycans show a strongly acidic reaction due to the uronic acids and the sulfuric ester groups. Some of these acidic groups are already naturally present, but they can also advantageously be introduced synthetically into the compounds, for example by sulfatation, to achieve the degree of sulfatation required by the invention. Suitable sulfatation methods which are mentioned in the literature are, for example, sulfatation with sulfuric acid and chlorosulfonic acid (U.S. Pat. Nos. 4,727,063, 4,948,881), sulfatation with chlorosulfonic acid in pyridine (Wolfrom et al., J. Am. Chem. Soc. 75 (1953), 1519) or Sulfatation with nitrous acid (Shively et al., Biochemistry 15 (18) (1976), 3932). Other methods are well-known to the person skilled in the art. Natural glycosaminoglycans, for example, such as heparin, heparan sulfate, keratan sulfate, dermatan sulfate, chondroitin or condroitin sulfate are employed for the sulfatation. The structure of heparan sulfate corresponds to that of heparin, but it has less N- and O-sulfate groups and more N-acetyl groups than heparin.

Glycosaminoglycans can advantageously be isolated from animal tissues, such as intestinal mucosa or from the ears of pigs or cattle. The tissues used for isolating the glycosaminoglycans are, for example, autolyzed and extracted with alkali. It is then possible to coagulate the protein and precipitate it, for example by acidification. After the precipitate has been taken up in a polar nonaqueous solvent such as ethanol or acetone, the fats are removed by extraction with an organic solvent. Finally, the proteins are removed by proteolytic digestion and thus the glycosaminoglycans are obtained. Charles et al. (Biochem. J. 30 (1936), 1927–1933) and Coyne, E. in Chemistry and Biology of Heparin (Elsevier Publishers, North Holland, N.Y., Lunblad, R. L., eds., 1981) describe methods for isolating heparin, for example.

These glycosaminoglycans isolated from natural sources may advantageously also undergo a derivatization, for example by polysulfatation, as described by way of example in U.S. Pat. No. 5,013,124, or as described above. This polysulfatation results in the glycosaminoglycans having a sulfur content of from 6 to 15% by weight. For the use according to the invention and/or for the pharmaceutical preparations, polysulfated glycosaminoglycans are selected which have a sulfur content of at least 12.5% by weight. Advantageously, these polysulfated glycosaminoglycans have a sulfur content of from 13 to 16% by weight, preferably from 13 to 15% by weight, particularly preferably from 13.5 to [lacuna] % by weight. These substances are used for producing pharmaceutical preparations which are suitable for inhibiting the γ-interferon-induced upregulation of the MHC Class I and MHC Class II proteins and ICAM-1. Preferably, these substances are employed in a physiologically effective amount for treating and preventing diseases which are associated with a γ-interferon-induced upregulation of the MHC class I and MHC Class II proteins and ICAM-1. Derivatives of the substances additionally mean compounds which improve the properties of the polysulfated glycosaminoglycans employed on use, in terms of their effect, their stability and their elimination from the body.

The glycosaminoglycans advantageously used are heparins and/or dermatan sulfate having an average molecular weight of from 1000 to 20,000 Dalton, preferably from 1500 to 9000 Dalton, particularly preferably from 2000 to 6000 Dalton. Low molecular weight polysulfated heparins and/or dermatan sulfates are particularly advantageous, in the form of the free acid or in the form of a salt with physiologically tolerated bases or mixtures of these compounds. These substances have a low anti-coagulant activity and are therefore particularly suitable for the treatment and prevention in the use according to the invention. Preferred salts of the polysulfated glycosaminoglycans are, for example, the sodium, calcium and magnesium salts.

Low molecular weight glycosaminoglycans, for example low molecular weight heparins and/or dermatan sulfates, can be prepared by a number of methods. The preparation of low molecular weight heparins by depolymerization using nitrous acid is described, for example, in EP-B-0 037 319 or in Biochemistry 15 (1976), 3932. Low molecular weight heparin or low molecular weight glycosaminoglycans can also be prepared using enzymes (Biochem. J. 108 (1968), 647). using sulfuric acid and chlorosulfonic acid (FR No. 2,538,404, simultaneous sulfatation), using periodate or using physical methods such as γ radiation (EP-A-0 269 937) or ultrasound (Fuchs et al., Lebensm. Unters. Forsch. 198 (1994), 486–490).

The invention further provides organoprotective solutions. By the advantageous addition of the polysulfated glycosaminoglycans to organoprotective solutions, it is possible to further improve storage of the organs after harvest from the donor organism, i.e. ex-vivo, by inhibiting the γ-interferon-induced upregulation of the MHC Class I and MHC Class II proteins and ICAM-1. It is advantageous to cool the organs, as known to the person skilled in the art.

A number of such solutions, as described above, is known from the literature. The solutions generally comprise salts, buffers, substances which are intended to stabilize the organs osmotically or to prevent oxidation, such as sugars or sugar alcohols, proteins, amino acids, lower carboxylic acids, purines, pyrimidines or pharmaceutically active compounds. Examples of such substances which may be mentioned are: raffinose, glucose, potassium dihydrogen phosphate, dipotassium hydrogen phosphate, potassium chloride, potassium hydrogen carbonate, sodium hydrogen carbonate, magnesium sulfate, magnesium chloride, adenosin, albumin, mannitol, citrate, verapamil, allopurinol, insulin, dexmethasone, hydroxyethyl starch, glutathione or glucuronic acid.

The use according to the invention in the organoprorective solutions makes it possible to transplant the organs in a better conditions, thus reducing rejections. To further reduce the risk of an organ resection, the polysulfated glycosaminoglycans can be administered orally or parenterally to the transplant patients prior to transplanation. Follow-up treatment of the patients with the substances is also feasible.

The organoprotective solutions or the other pharmaceutical preparations comprise the polysulfated glycosaminoglycans in amounts of from 10 mg/l to 10,000 mg/l, advantageously in amounts of from 10 mg/l to 5000 mg/l, preferably in amounts of from 50 mg/l to 3000 mg/l and particularly preferably in amounts of from 100 mg/l to 3000 mg/l. In addition, the organoprotective solutions or the other pharmaceutical preparations comprise from 5 to 100 g/l of an osmolytically stabilizing substance, advantageously hydroxyethyl starch.

Other advantageous organoprotective solutions have the following composition: a) from 10 mg/l to 10,000 mg/l of polysulfated glycosaminoglycans having a sulfur content of at least 12.5% by weight, from 5 to 100 g/l of hydroxyethyl starch and from 5 to 100 mmol of raffinose or b) from 10 mg/l to 10,000 mg/l of polysulfated glycoseaminoglycans having a sulfur content of at least 12.5% by weight, from 5 to 100 g/l of hydroxyethyl starch, from 5 to 100 mmol of raffinose, from 5 to 40 mmol of $KH_2PO_4$, from 1 to 50 mmol of $MgSO_4$, from 1 to 50 mmol of adenosine, from 0.5 to 5 mmol of allopurinol or from 1 to 10 mmol of glutathione.

For treating the patients, the polysulfated glycosaminoglycans can be employed together with customary formulation auxiliaries. The pharmaceutical preparations used according to the invention can be administered in a conventional way orally or parenterally (subcutaneously, intraveneously, intramuscularly, intra-peritoneally), and oral or intravenous administrations are preferred.

The dosage depends on the age, condition and weight of the patient and on the mood of administration.

The glycosaminoglycans are advantageously administered in a dose of from 0.1 to 500 mg/kg of bodyweight/day. In the case of parenteral use, the glycosaminoglycans are advantageously administered in a dose of from 0.1 to 30 mg/kg of bodyweight/day, and in the case of oral use they are administered in a dose of from 0.2 to 500 mg/kg of bodyweight/day, it being possible to administer the dose in a single dose or in divided doses. Mixtures of, for example, at least one low molecular weight heparin and/or its polysulfated derivative and/or at least one low molecular weight dermatan sulfate and/or its polysulfated derivative are also administered in a dose of from 0.1 to 30 mg/kg of bodyweight/day on parenteral administration or in a dose of from 0.2 to 500 mg/kg/day on oral administration.

Pharmaceutical preparations comprising the polysulfated glycosaminoglycans for the treatment and prevention of diseases associated with organ transplants are in principle all pharmaceutical administration forms which can be used for oral or parenteral administration, whether solid or liquid, such as uncoated or (film-)coated tablets, capsules, powders, granules, suppositories, solutions or suspensions. They are produced in a conventional way. The active compounds can moreover be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991), The administration forms obtained in this way normally contain from 0.1 to 90% by weight of the active compound.

To produce uncoated or (lacquer-)coated tablets and hard gelatin capsules, the polysulfated glycosaminoglycans can also be processed with pharmaceutically inerts, inorganic or organic excipients. Excipients which can be used for uncoated or coated tablets and hard gelatin capsules are lactose, corn starch or derivatives thereof, talc, stearic acid or its salts. Excipients suitable for soft gelatin capsules are vegetable oils, waxes, fats, semisolid and liquid polyols.

Excipients suitable for producing solutions and syrups are, for example, water, polyols, sucrose, invert sugar, glucose and the like. Excipients suitable for solutions for injection are water, alcohols, polyols, glycerol, vegetable oils. Excipients suitable for suppositories are natural or hardened oils, waxes, fats, semiliquid or liquid polyols and the like.

The pharmaceutical preparations may moreover comprise preservatives, solubilizers, stabilizers, wetting agents, emulsifiers, sweeteners, colorants, flavorings, salts to alter the osmotic pressure, buffers, coating agents and/or antioxidants.

EXAMPLES

Proximal tubular epithelial cells were cultured according to the methods described by Detrisac et al. (25). In short: PTEC were grown on tissue culture flasks that had been coated with collagen I (Sigma St. Louis Mo.) and Foetel Calf Serum (FCS, from Gibco BRL). The culture medium consisted of Dulbecco's eagle's medium and Ham's medium (both from Gibco BRL) in a 1:1 ratio, supplemented with insulin (5 $\mu$l/ml), transferrin (5 $\mu$g/ml), selenium (5 ng/ml), hydrocortisone (36 ng/ml), triiodothyronine (4 pg/ml) epidermal growth factor (10 ng/ml), and penicillin/streptomycin (5 IE/ml, 5 $\mu$g/ml) (all from Sigma). The cell lines were acquired from multiple sources including biopsy tissue pretransplant, allografts unsuitable for transplantation and from grossly normal surgical nephrectomy specimens. Experiments were performed using cells from passages one to four. PTEC were characterized by positive staining for the epithelial membrane antigen (EMA, Dako Glostrup Denmark) and the adenosinedeaminase binding protein (kindly provided by Dr. Dinjens, University Hospital Maastricht, the Netherlands).

Human umbilical vein endothelial cells were prepared from fresh umbilical cord using the methods described by Jaffe et al (26). Briefly, endothelial cells were isolated from umbilical veins by digestion with collagenase V (Sigma, St. Louis Mo.) for 20 minutes at 37° C. Thereafter the vein was flushes with sterile medium to collect endothelial cells. The culture medium consisted of Medium 199 (Gibco BRL) supplemented with 1% FCS, Endothelial Cell Growth Factor and antibiotics (penicillin-streptomycin). The cells were cultured in 25 cm$^2$ flasks that had been coated with 1% gelatine (Sigma, St. Louis Mo.).

All experiments were performed with cells from passage three to six. HUVEC were characterized on the basis of positive staining for factor VIII-related antigen (Dako, High Wycombe, UK) and the endothelial marker EN4 (CD31).

IFN-γ Stimulation, Heparin and Sodium Chlorate Treatment

Confluent monolayers of PTEC or HUVEC were trypsinized and seeded in 24-well plates. Upon confluency the cells were stimulated with IFN-γ (Sigma, St. Louis Mo.) for 72 g in the presence or absence various concentrations of heparinoids in various Heparin (Heparin-Braun®) was purchased from Braun Melsungen (Melsungen, Germany), low molecular weight heparin (Fragmin® P) from Pfrimmer Kabi (Erlangen, Germany), and modified low molecular weight heparins (Knoll AG Ludwigshafen, Germany).

In some experiments the culture medium was supplemented with sodium chlorate in order to inhibit sulfation of cellbound HSPG. Chlorate was used in concentrations between 50 to 150 mM for 24 hours before addition of IFN-γ and was present during the stimulation period. Sodium chloride was used as osmolarity control. Cultured cells were recovered by brief treatment with trypsin-EDTA for flow cytometry analysis.

Flow Cytometry Analysis

Cells were pooled, divided into two tubes and washed. Isotype matched irrelevant antibodies conjugated to RPE and FITC (from Dako, Glostrup, Denmark) and Cy-5 (from Dianowa, Hamburg, Germany) were added to the first tube which was used as negative control for the FACS settings. Cells from the second tube were labelled with antibodies against MHC class I (RPE-conjugated, W6, 32, Dako), MHC class II (Cy-5-conjugated, CR3/43, Dianova) and ICAM 1 (FITC-conjugated, Dianova) in concentrations according to the instructions of the manufacturer. After incubation for 30 min at 4° C. the cells were washed and analysed by flow cytometry (FACScan, Becton Dickinson); a minimum of 10000 event were analysed. The results are expressed as mean fluorescence intensity (MFI).

Dotblot Analysis

Small strips of nitrocellulose membranes were prepared and 1 μl of heparin, fragmin and the carious GAGS (all in a concentration of 1 mg/ml) were applied onto the strip. After air drying, the strips were fixed in 1% glutaraldehyde +0.5% cetylpyridinium chloride to prevent GAG loss and washed in Tris buffer. The non-occupied protein binding sites were blocked with 5% BSA in PBS for 30 min at 37° C. The strips were subsequently incubated with $^{125}$I IFN-γ for 1 hour at 4° C. in the presence or absence of heparin. Hereafter the strips were extensively washed with Tris buffer and exposed to a Kodak film.

Statistical Analysis

The significance of changes in antigen expression was assessed by application of Student's t-test. P-values <0.05 were considered to be significant.

Results

The expression of MHC class I, class II and ICAM-1 on PTEC is modulated by IFN-γ in a dose dependent fashion. MHC class I and ICAM-1 expression was already upregulated using a concentration of 50 ng/ml of IFN-γ. In addition, MHC class II expression was induced on PTEC with the same concentration of IFN-γ (FIG. 1). Similar results were obtained with cultured HUVEC (data not shown).

Figure 2:
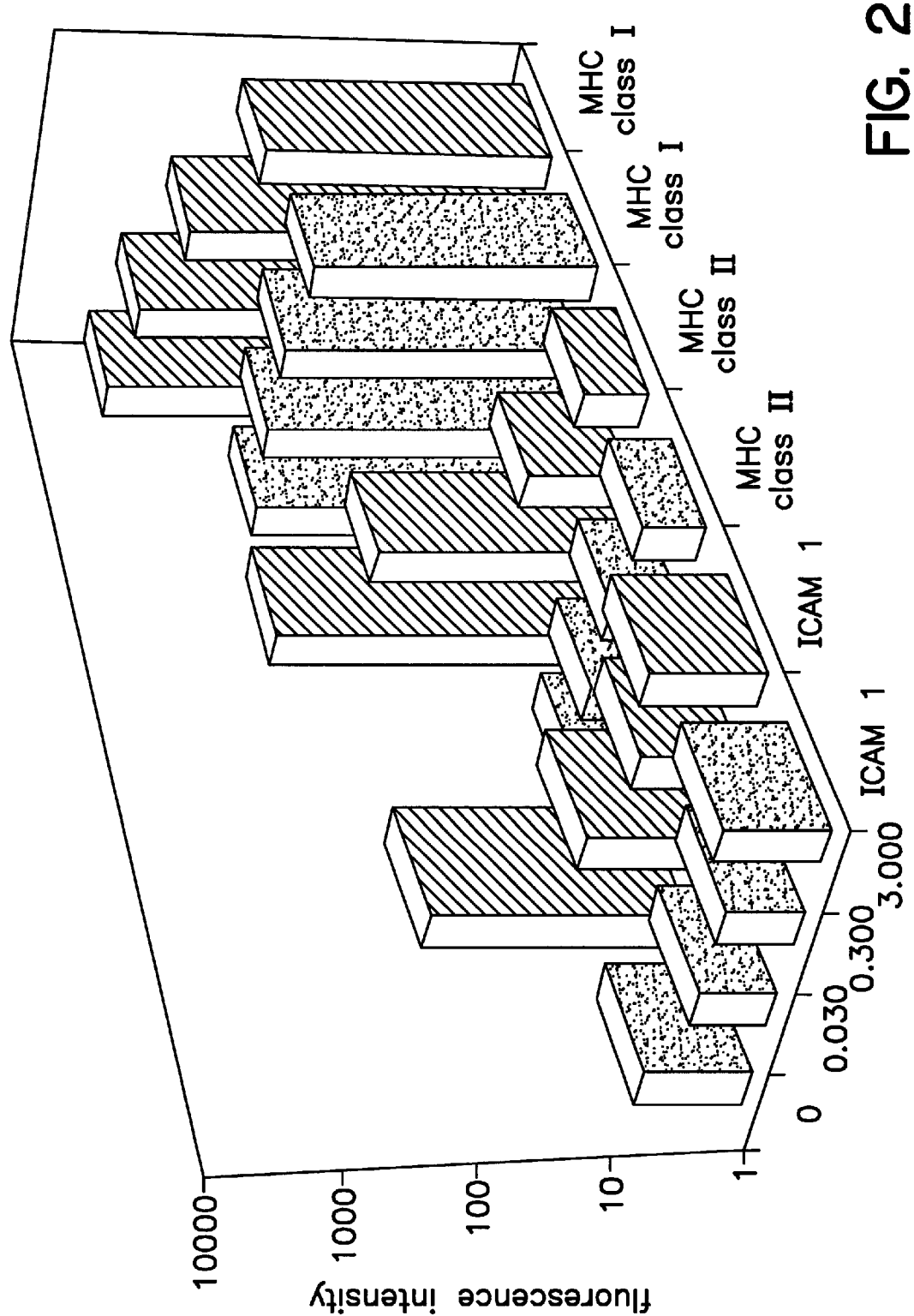
FIG. 2 shows the effect of heparin on MHC and ICAM-1 expression on IFN-γ stimulated HUVEC.

In order to investigate the influence of heparin on the ability of IFN-γ to modulate the MHC and ICAM-1 expression, both HUVEC and PTEC cultures were stimulated with IFN-γ in the presence or absence of heparin. Addition of heparin in concentrations ranging from 0.03 to 3 mg/ml to HUVEC cultures completely abolished the upregulation of MHC class I and ICAM-1 by 100 ng/ml of IFN-γ. Moreover, heparin was able to inhibit the induction of MHC class II on these cells. Heparin itself, in the absence of IFN-γ, had no influence on the expression of all three antigens tested (FIG. 2).

Figure 3A:
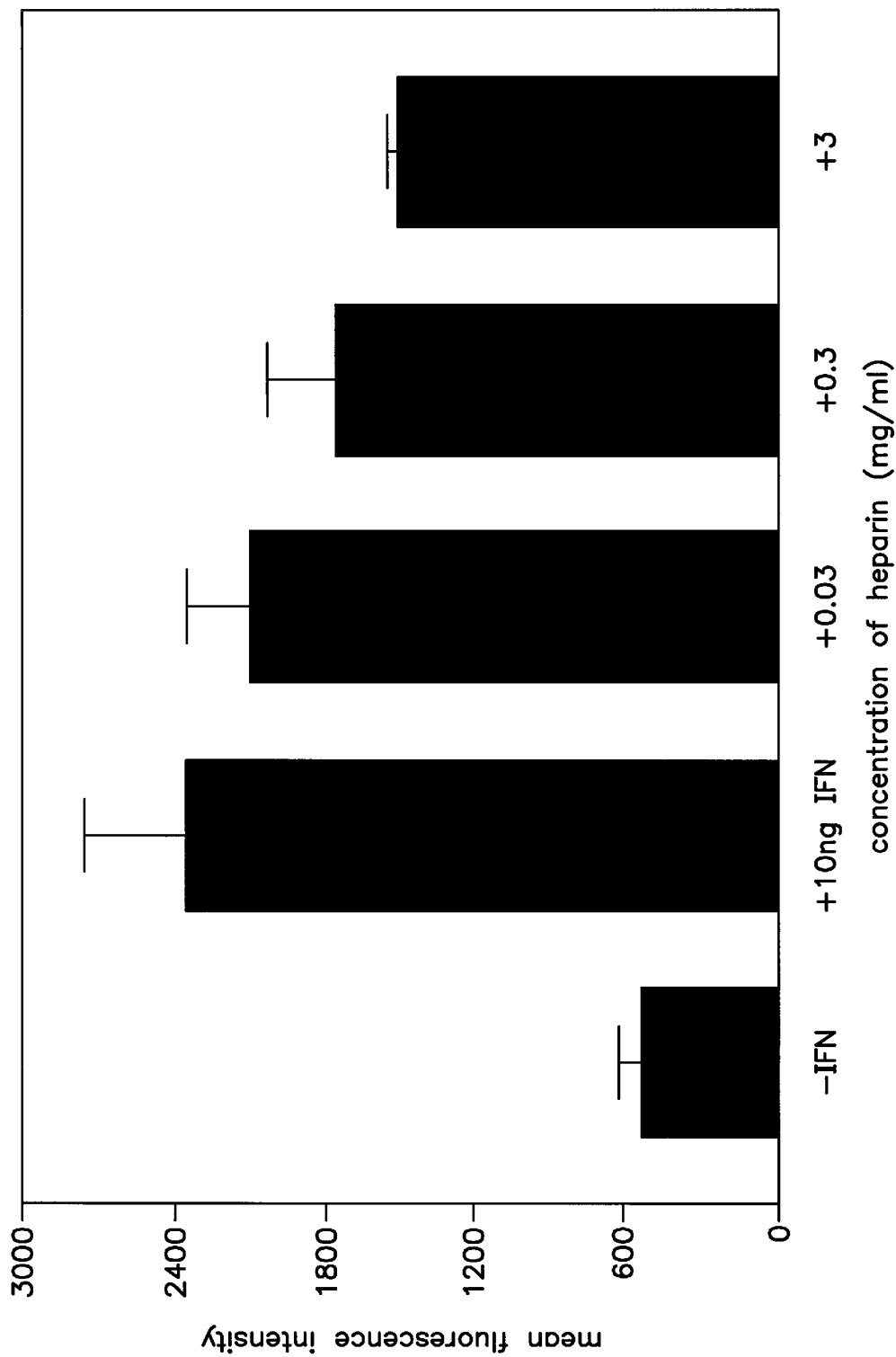
FIG. 3 shows the effect of heparin on MHC and ICAM-1 expression on IFN-γ stimulated PTEC.
Figure 3B:
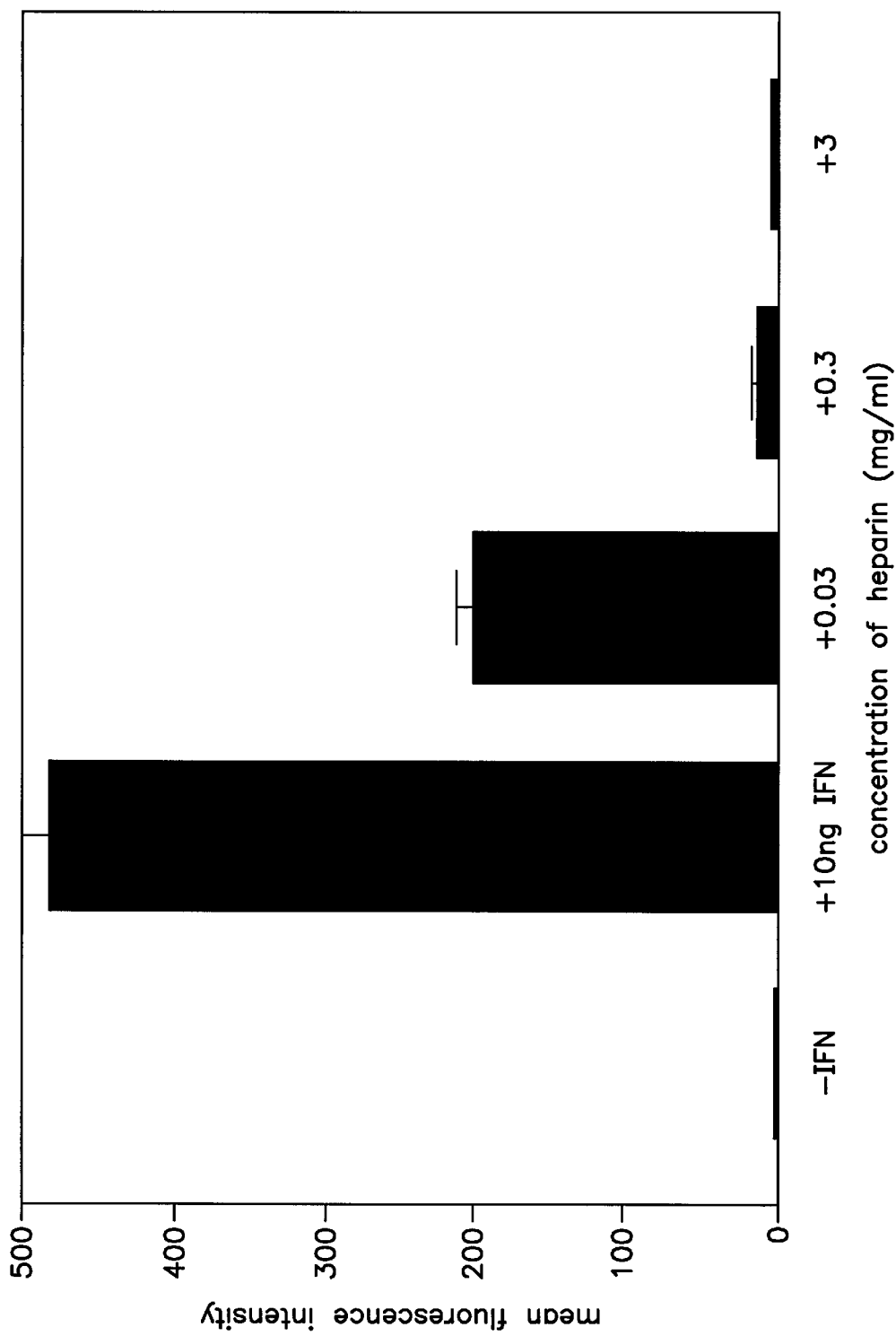
Figure 3C:
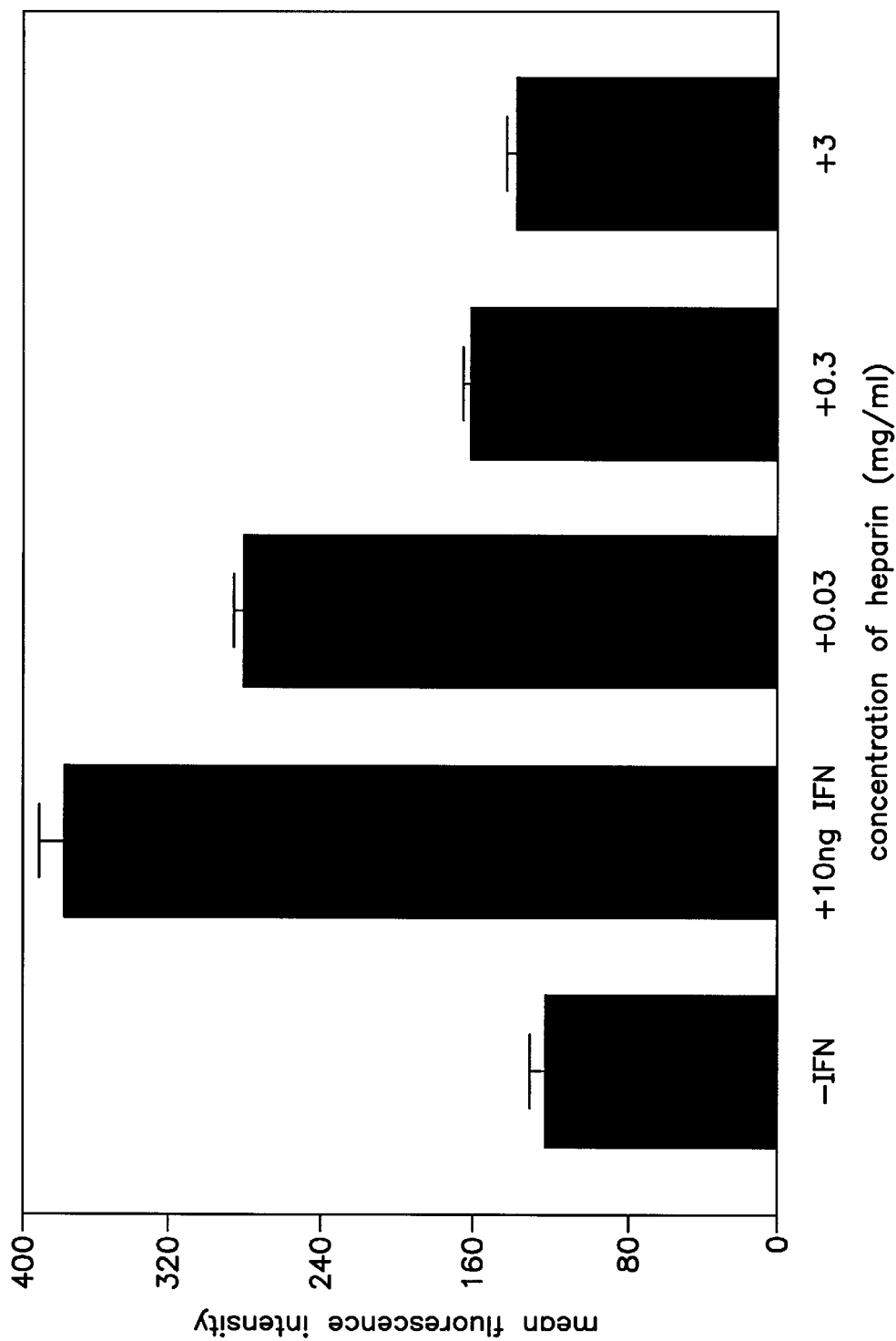

In similar experiments using PTEC, we could demonstrate that heparin was able to inhibit the upregulation of ICAM-1 and the induction of MHC class II by 100 ng/ml of IFN-γ. However, the upregulation of MC class I by IFN-γ, was not influenced by heparin. To test whether the upregulation of MHC class I by low concentrations of IFN-γ could be inhibited by heparin, the same experiments were performed using only 10 ng/ml of IFN-γ to stimulate the cells. Even at concentrations of 3 mg/ml, heparin had only a marginal influence on the upregulation of MHC glass I by IFN-γ (FIG. 3a). In contrast, both the induction of MHC class I and the upregulation of ICAM-1 were significantly inhibited by 0.03 mg/ml of heparin (p<0.01) (FIG. 3b and c).

Figure 4A:
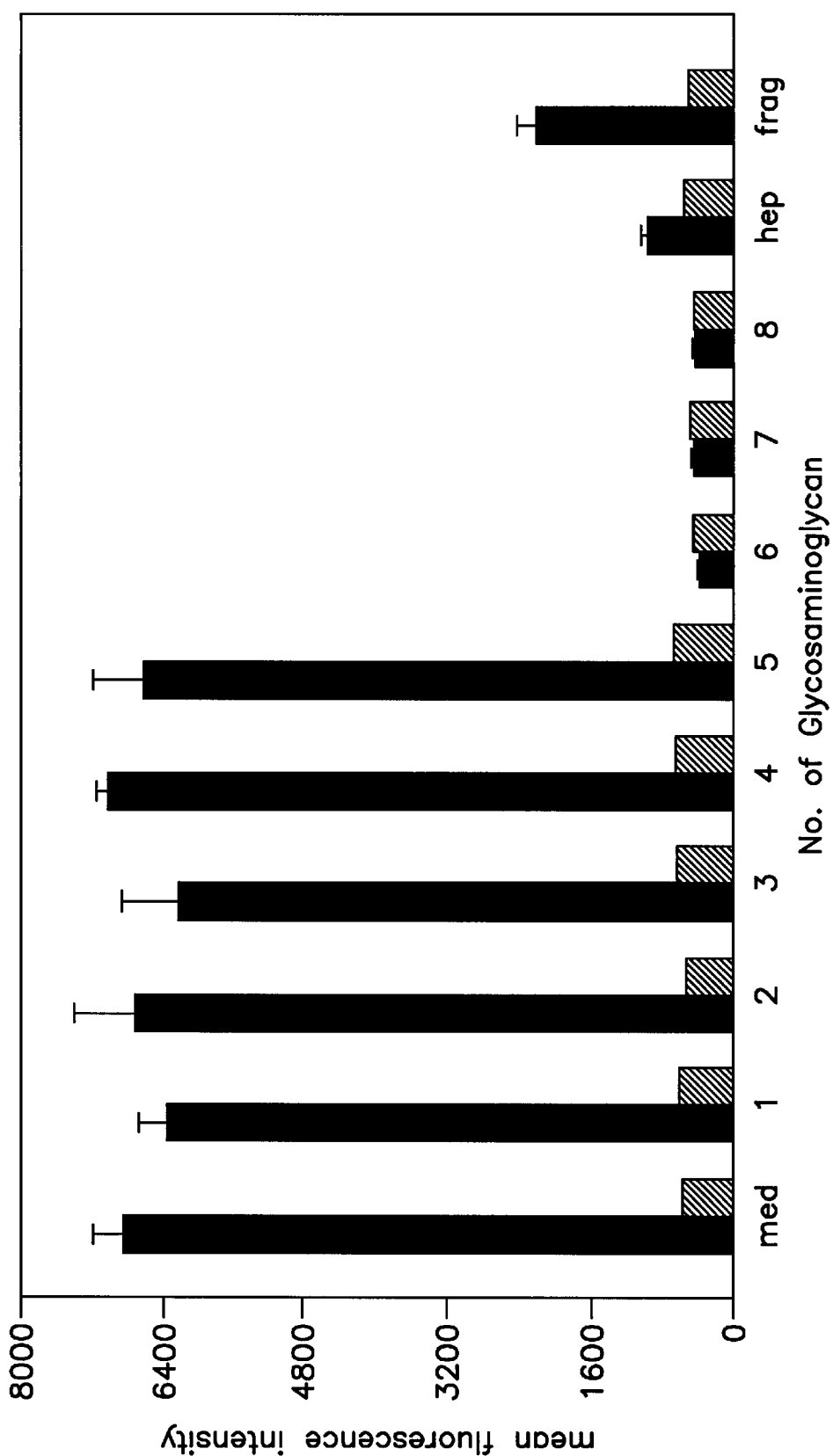
FIG. 4 shows the effect of different heparins and glycosaminoglycans on MHC and ICAM-1 expression on IFN-γ stimulated HUVEC.
Figure 4B:
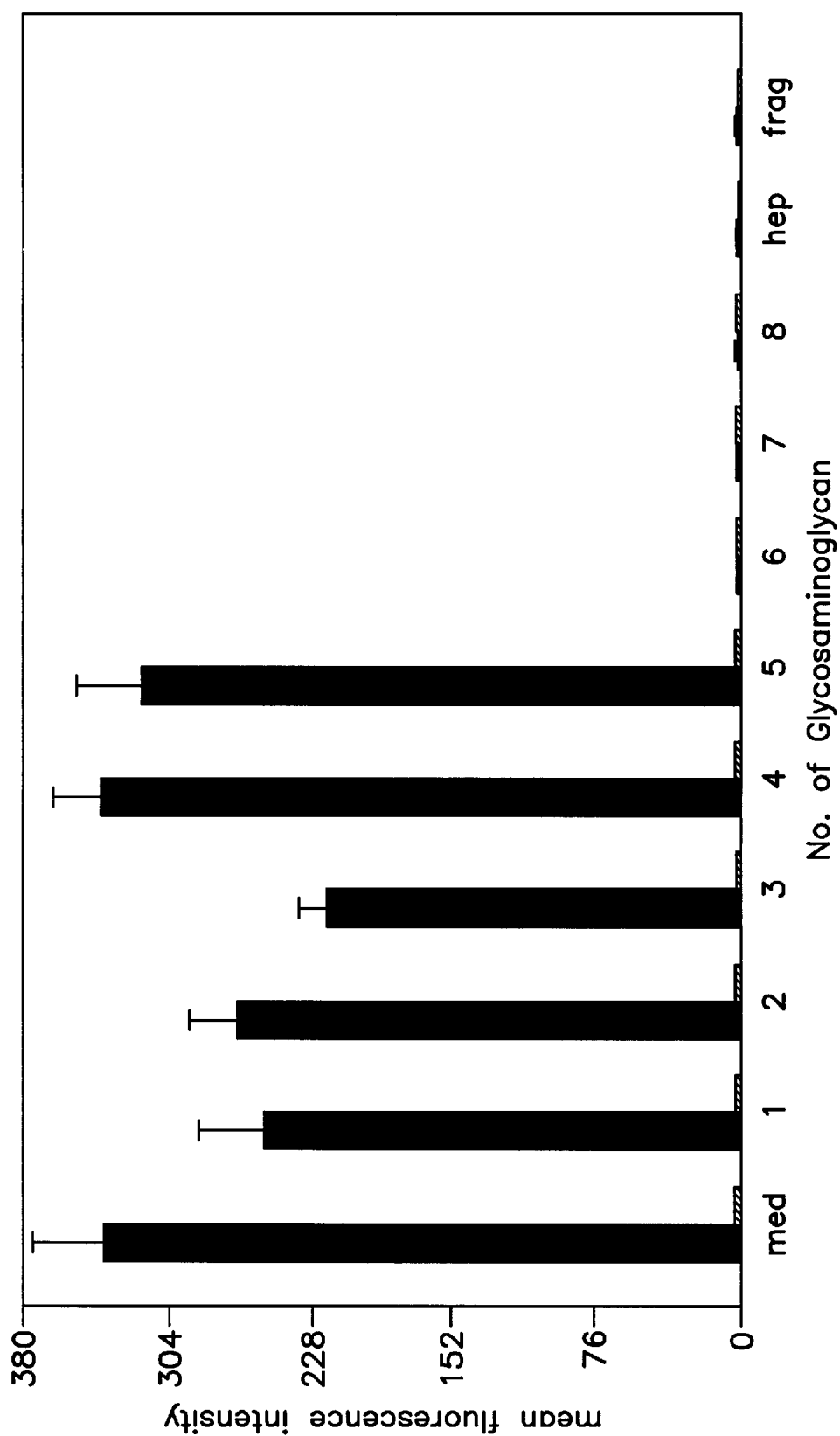
Figure 4C:
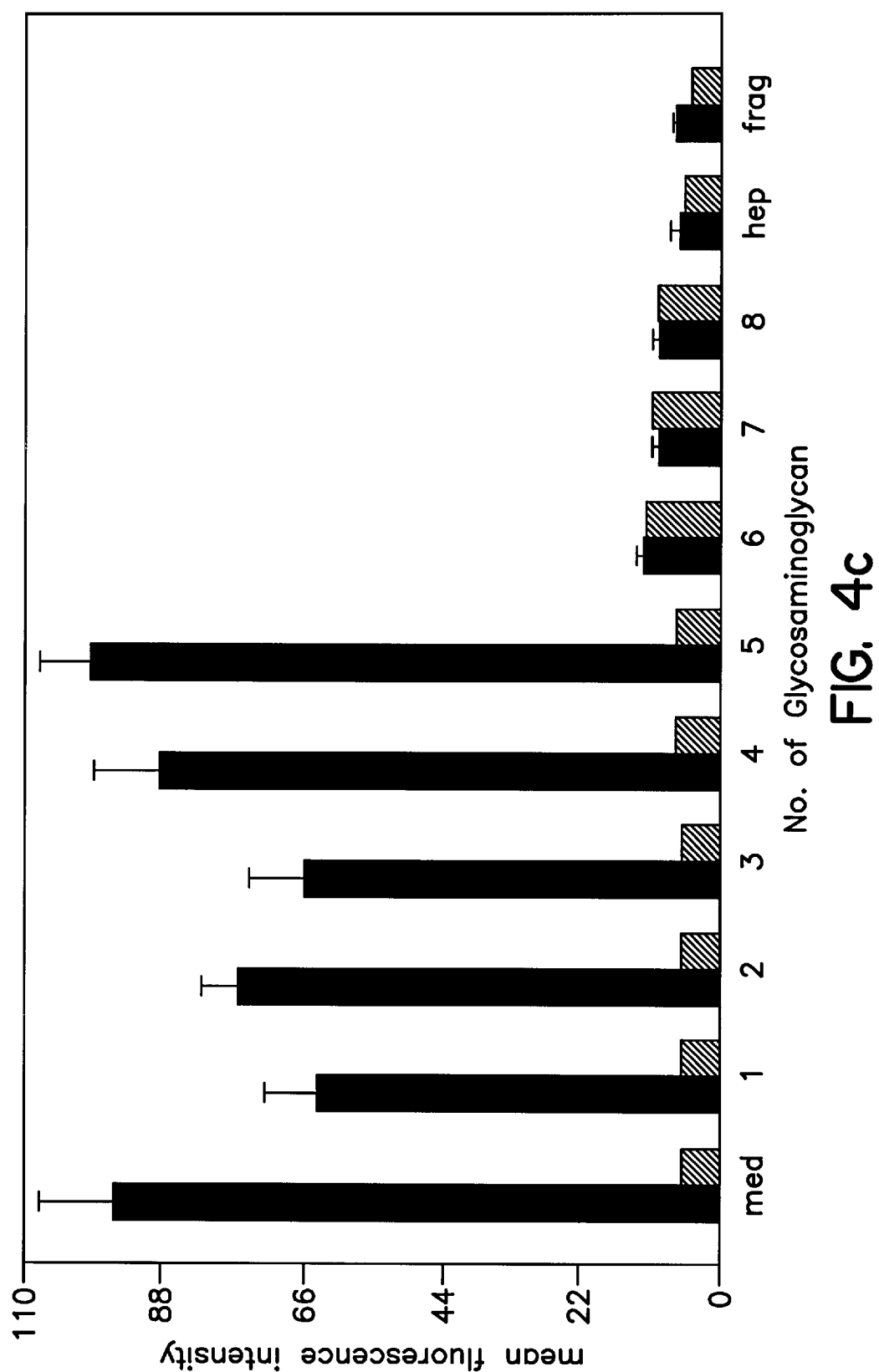
Figure 5A:
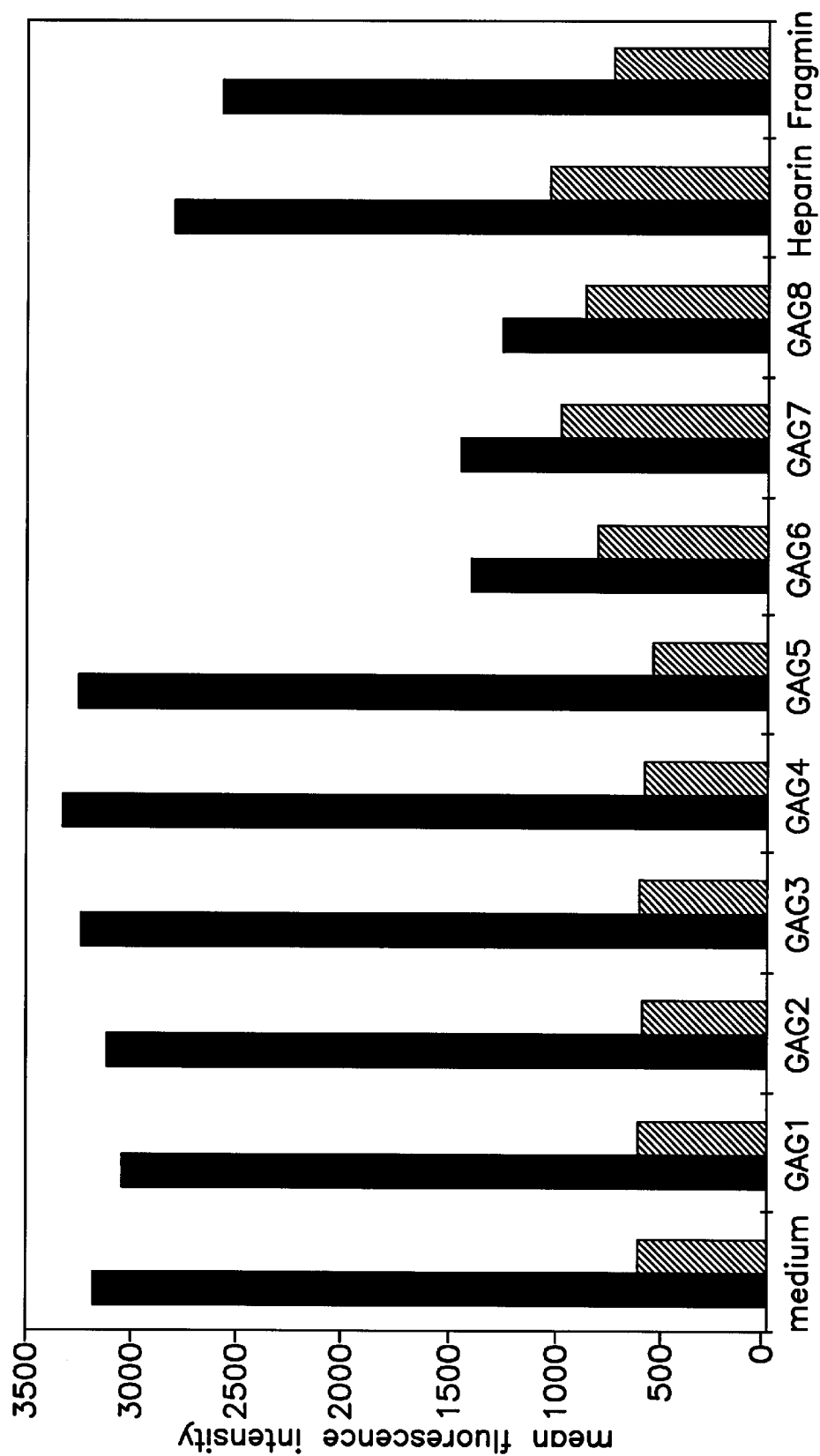
FIG. 5 shows the effect of different heparins and glycosaminoglycans on MHC and ICAM-1 expression on IFN-γ stimulated PTEC.
Figure 5B:
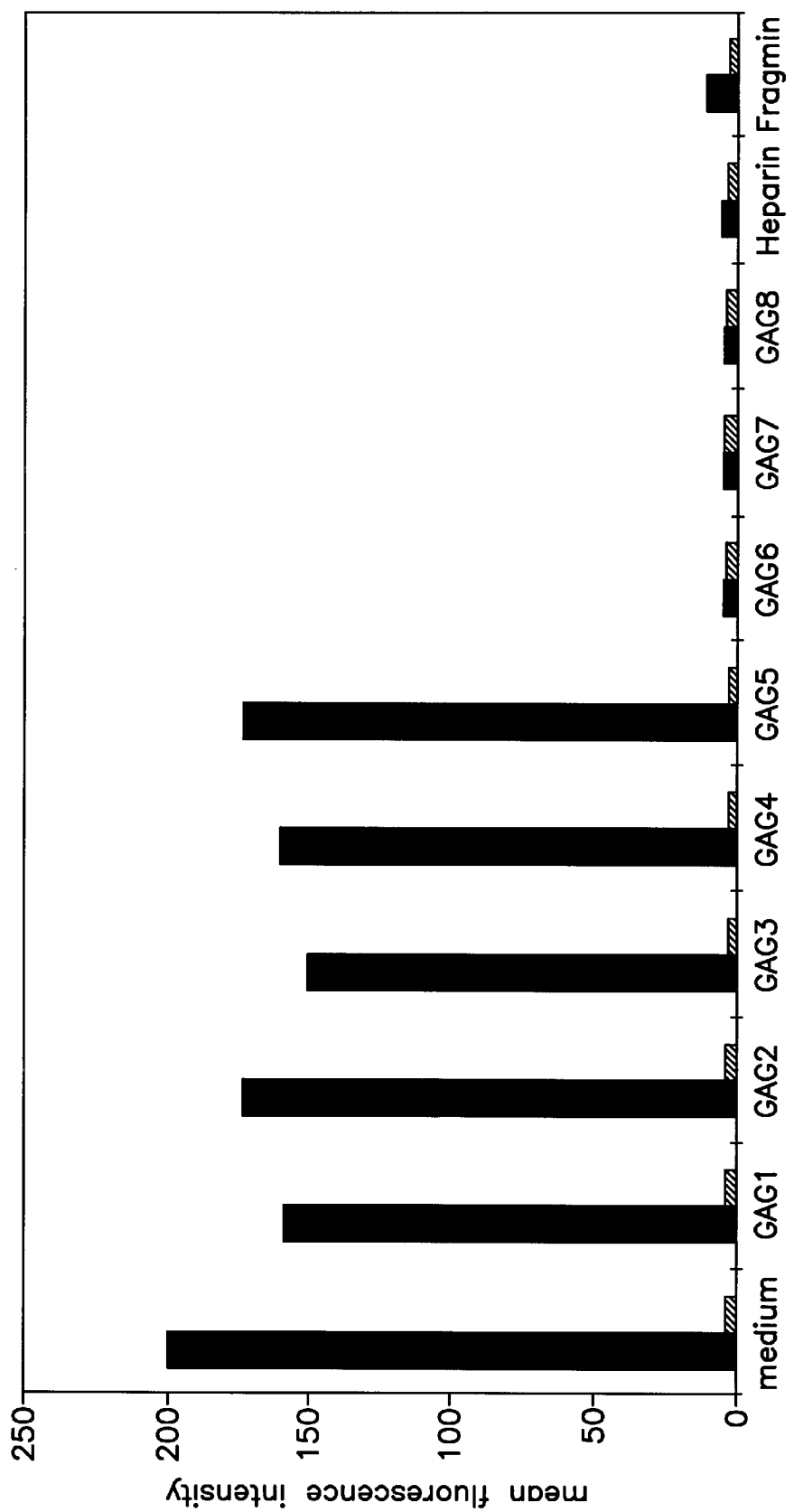
Figure 5C:
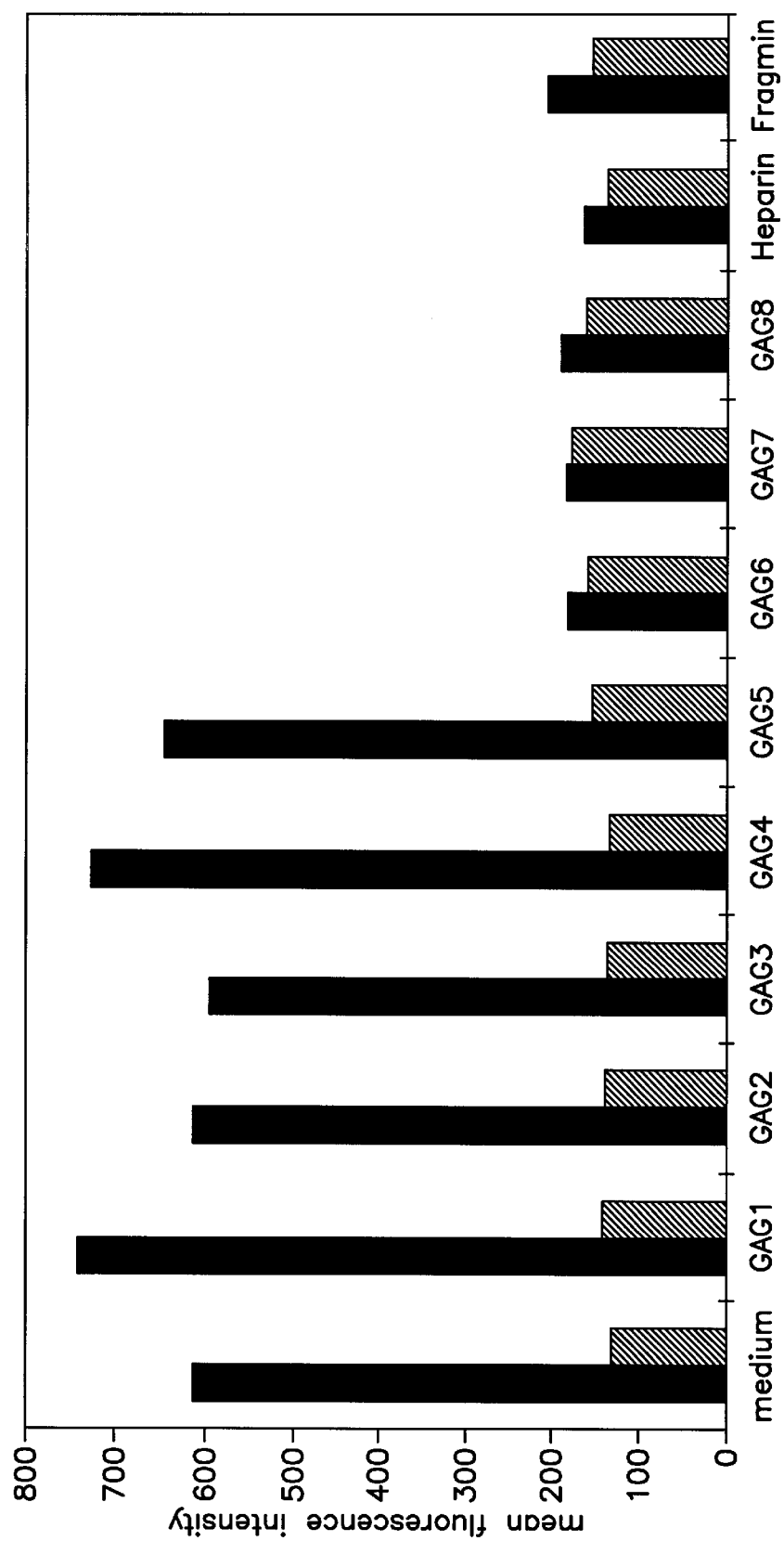
Figure 6A:
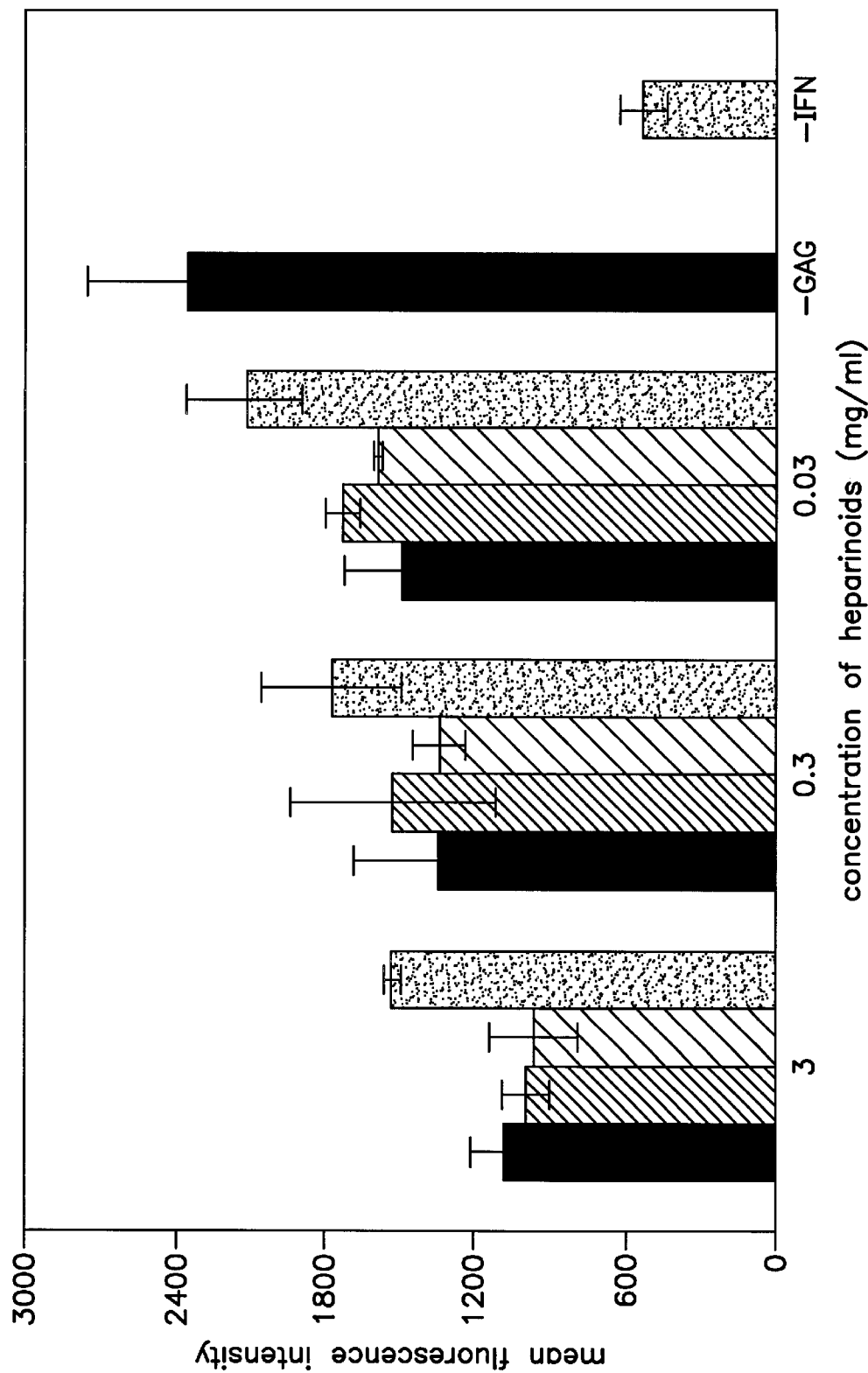
FIG. 6 shows a comparison between GAG 6–8 and heparin for their ability to inhibit MHC and ICAM-1 expression on IFN-γ stimulated PTEC.
Figure 6B:
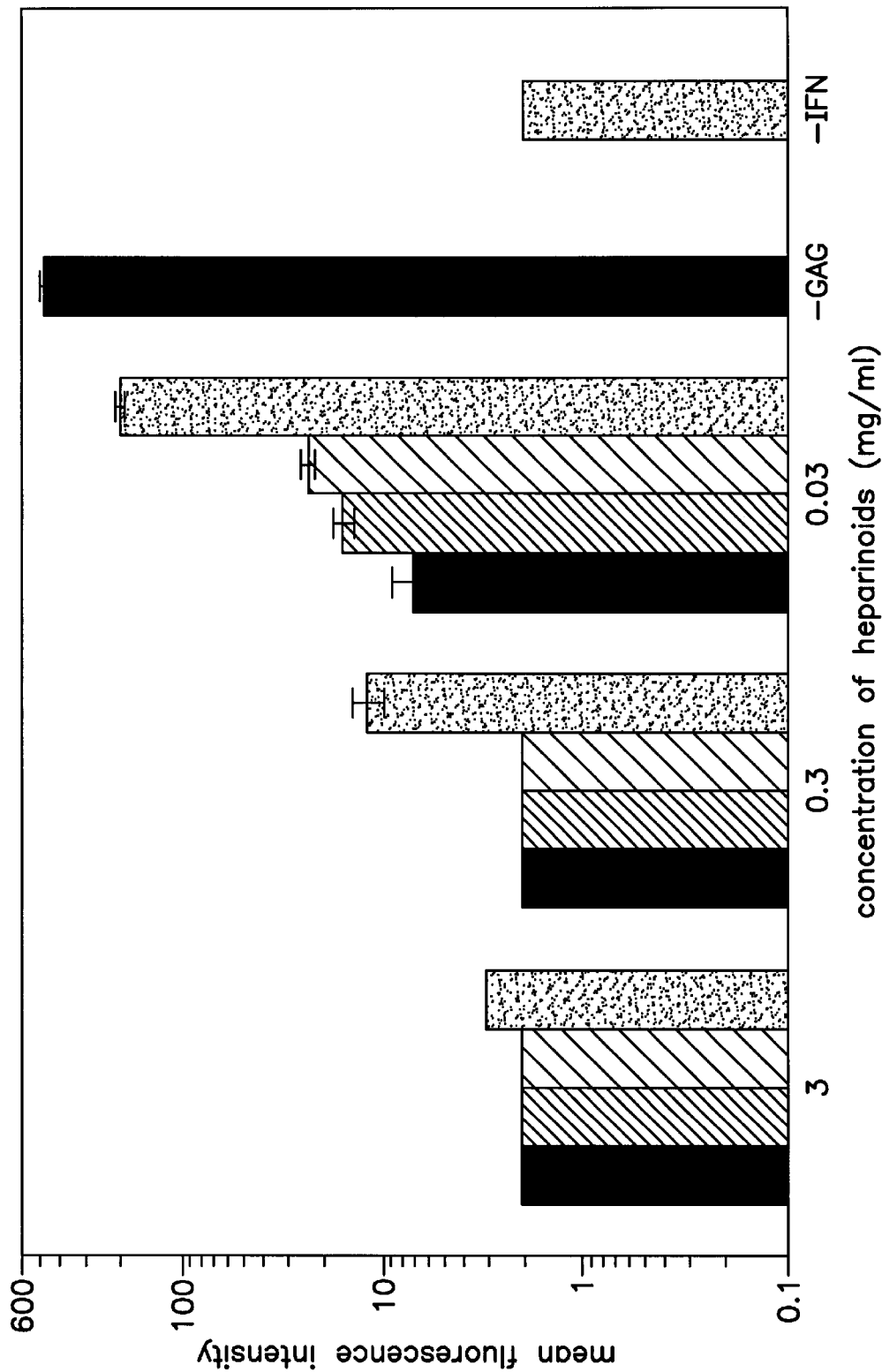
Figure 6C:
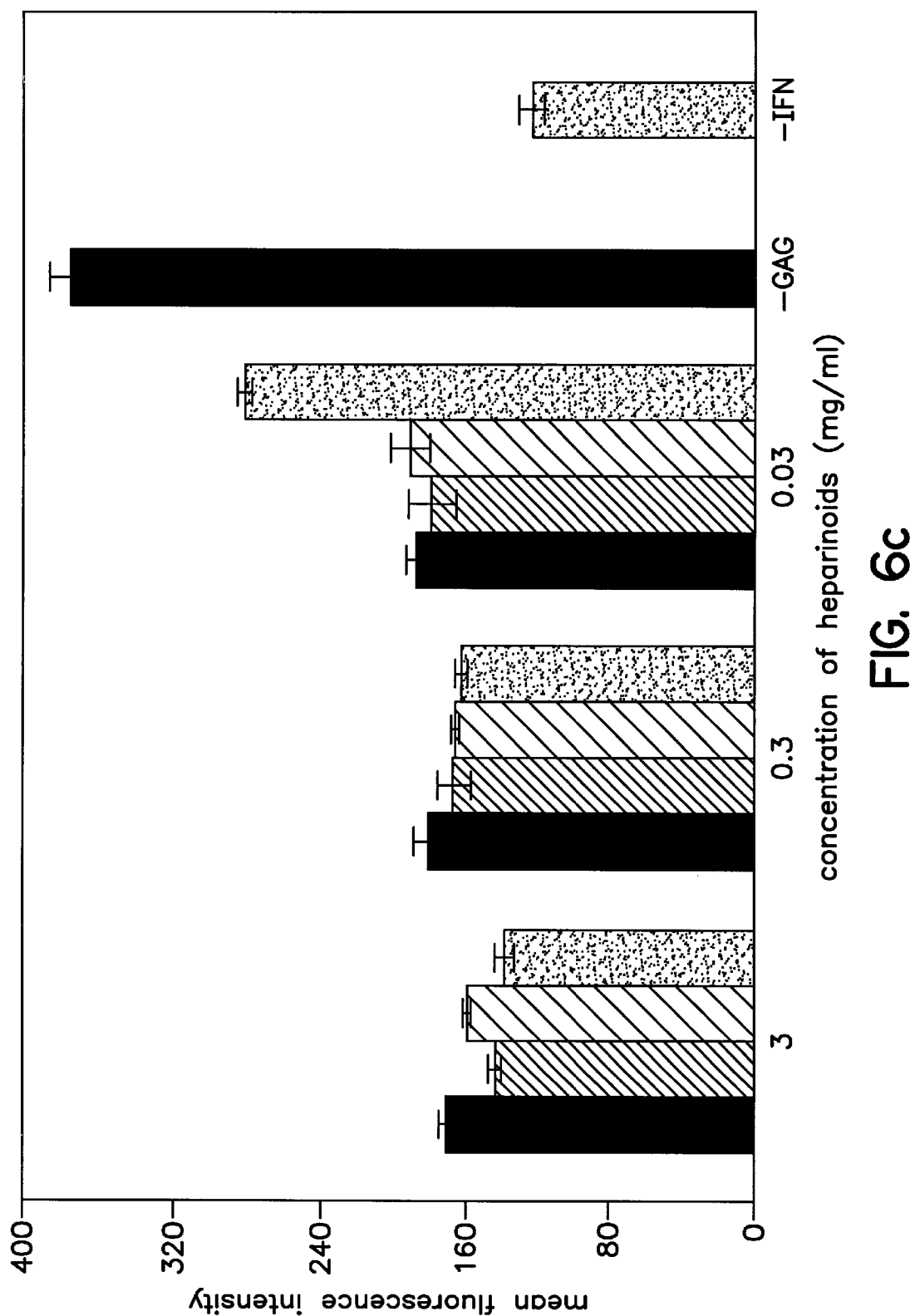

To determine whether the degree of sulfation of heparin is relevant for the inhibition of MHC and ICAM-1 expression after IFN-γ stimulation, various heparinoids were compared in this model (table 1). The heparinoids were all tested in a concentration of 3 mg/ml for their ability to inhibit the upregulation of MHC class I and ICAM-1 and the induction of MHC class II respectively by 10 ng/ml of IFN-γ. Similar to normal and low molecular weight heparin, supersulfated GAG (GAG 6–8) were able to inhibit MHC and ICAM-1 expression on both HUVEC and PTEC after IFN-γ stimulation. In contrast, desulfated-N-acetylated GAG (GAG 1–5) were not able to influence MHC and ICAM-1 expression on these cells after IFN-γ stimulation (FIGS. 4 and 5). There was a tendency that supersulfated GAG were more effective in the inhibition of MHC class I expression after IFN-γ stimulation in comparison to normal and low molecular heparin. This was more pronounced in PTEC cultures (FIG. 5a). To further substantiate this latter finding, dose-response experiments with low molecular heparin and GAG 68 were performed using PTEC that had been stimulated with 10 ng/ml of IFN-γ. Whereas the addition of GAG 6–8 in a concentration of 0.03 mg/ml to IFN-γ stimulated cultures had a significant inhibitory effect on MC and ICAM-1 expression (p<0.05), heparin did not significantly inhibit MHC class I and class II expression ICAM-1 expression was significantly inhibited by heparin, although to a smaller extend than GAG 6–8 (FIG. 6). These results thus demonstrate that supersulfated GAG are more effective in the inhibition of MHC and ICAM-1 expression after IFN-γ stimulation compared to heparin.

Figure 7A:
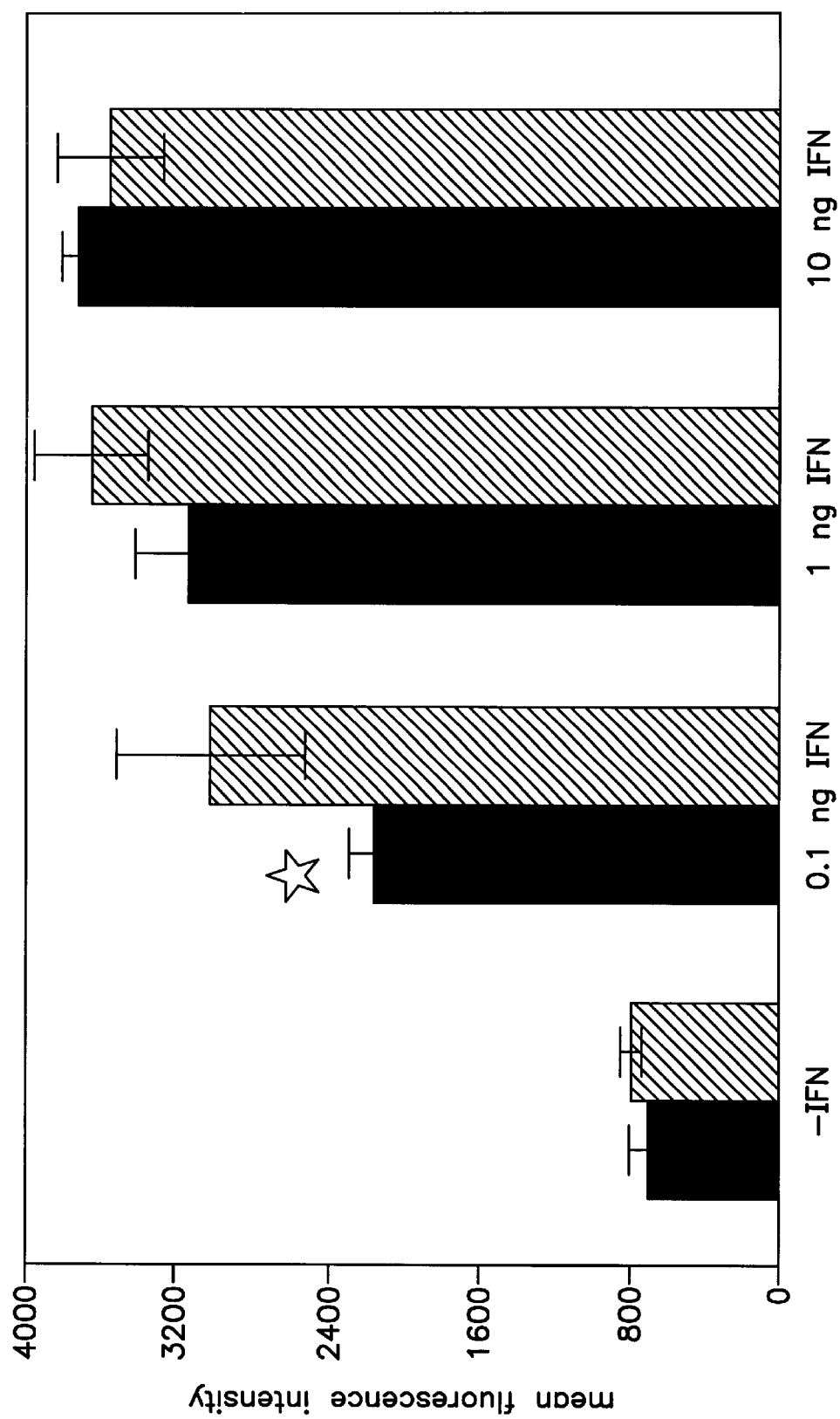
FIG. 7 shows the effect of NaClO$_3$ on the capacity of IFN-γ to stimulate MHC and ICAM-1 expression on PTEC.
Figure 7B:
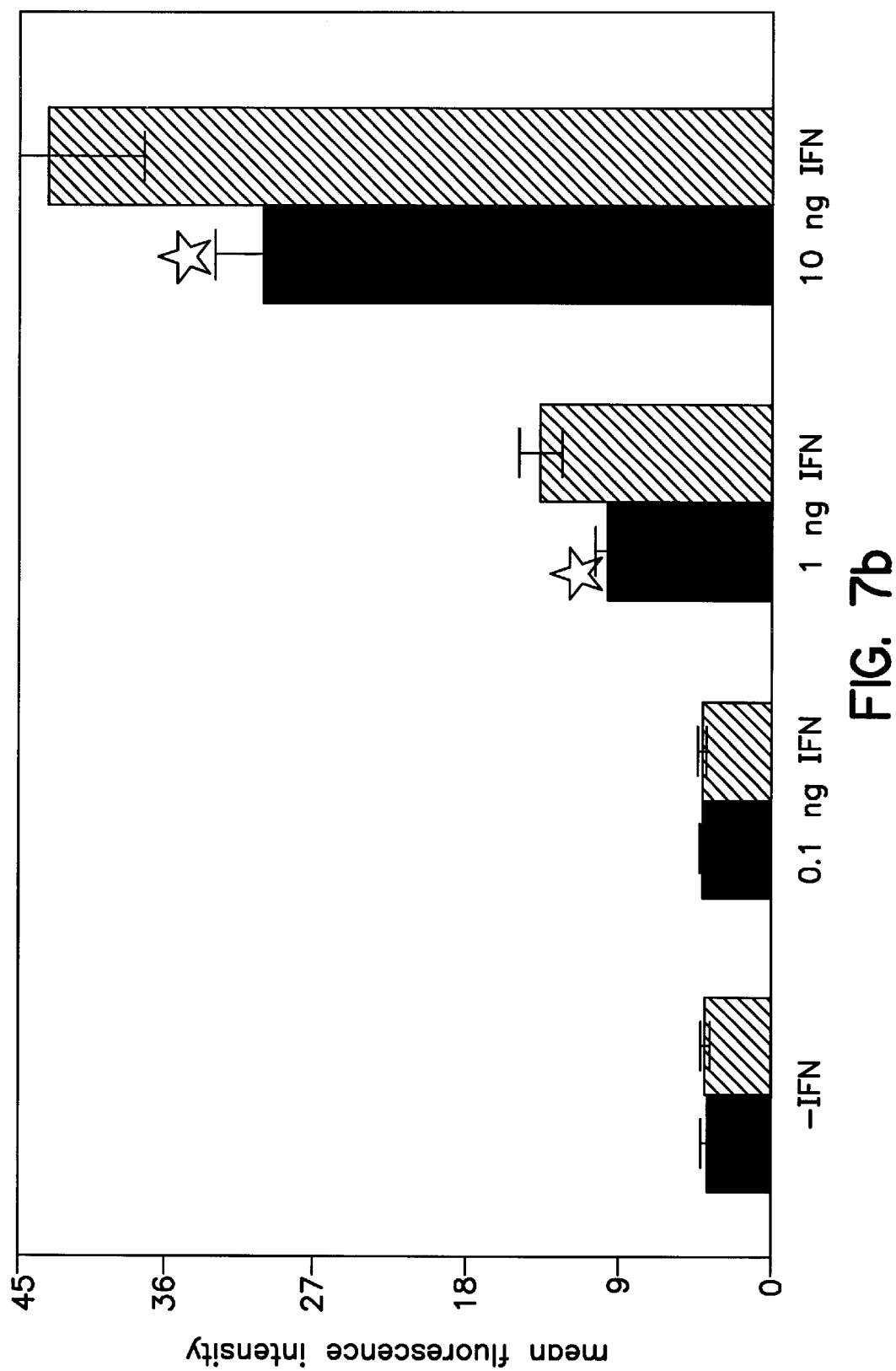
Figure 7C:
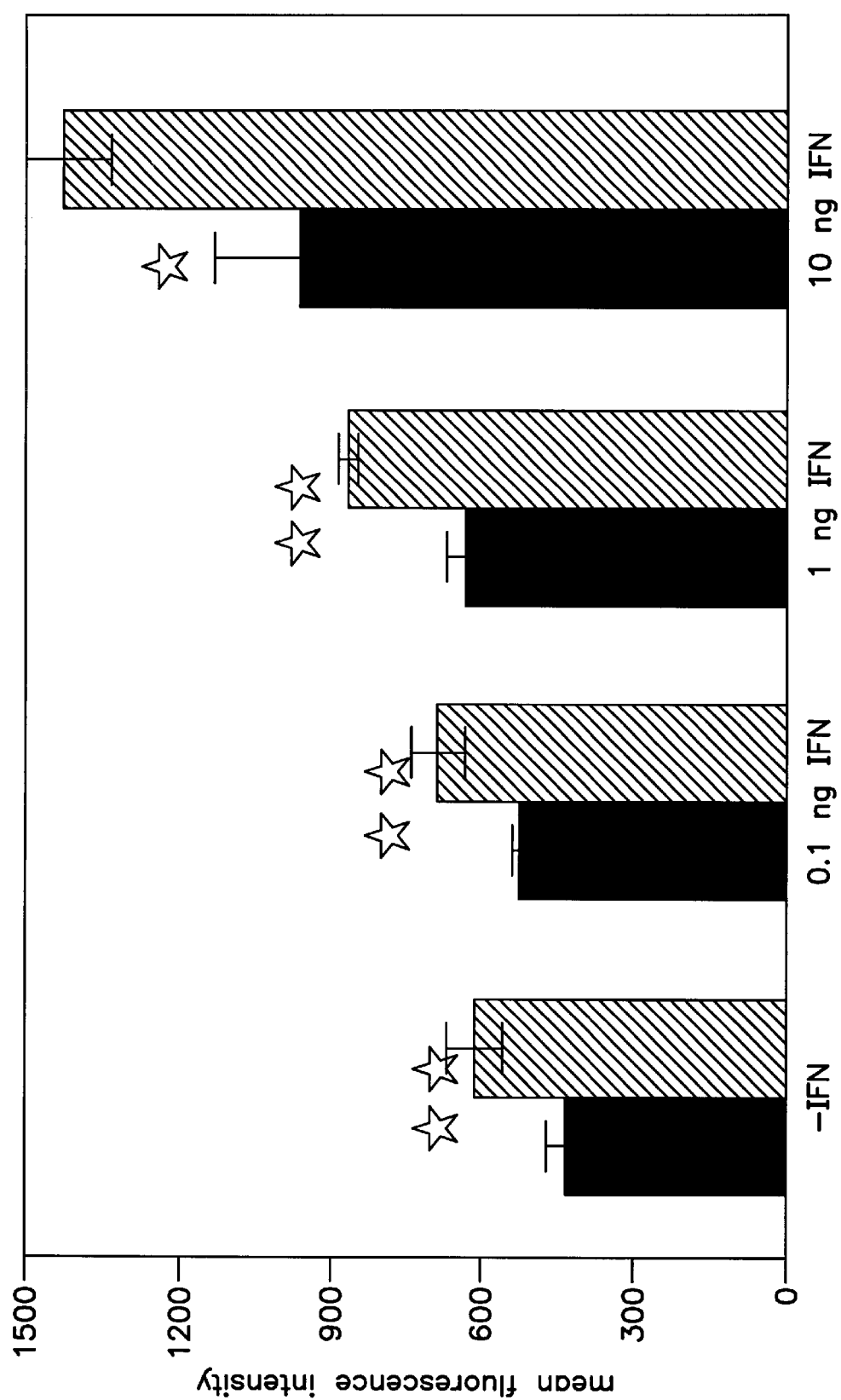

Since these studies suggested that sulfation of GAG is of importance to exert an inhibitory effect on MHC and ICAM-1 expression after IFN-γ stimulation, we addressed the question whether sulfation of cellbound HSPG is required for IFN-γ to modulate MHC and ICAM-1 expression. To this end, PTEC were cultured in the presence of NaClO$_3$ to prevent sulfation of HSPG, or in the presence of an equimolar concentration of NaCl as control and subsequently stimulated with IFN-γ in concentrations ranging from 0 to 10 ng/ml. Although IFN-γ was till able to modulate MHC and ICAM-1 expression on NaClO3 treated PTEC, this was significantly reduced in comparison to NaCl treated cultures (FIG. 7), suggesting a role for sulfated groups of HSPG in the effectivity of IFN-γ to modulate the expression of these antigens.

Figure 8:
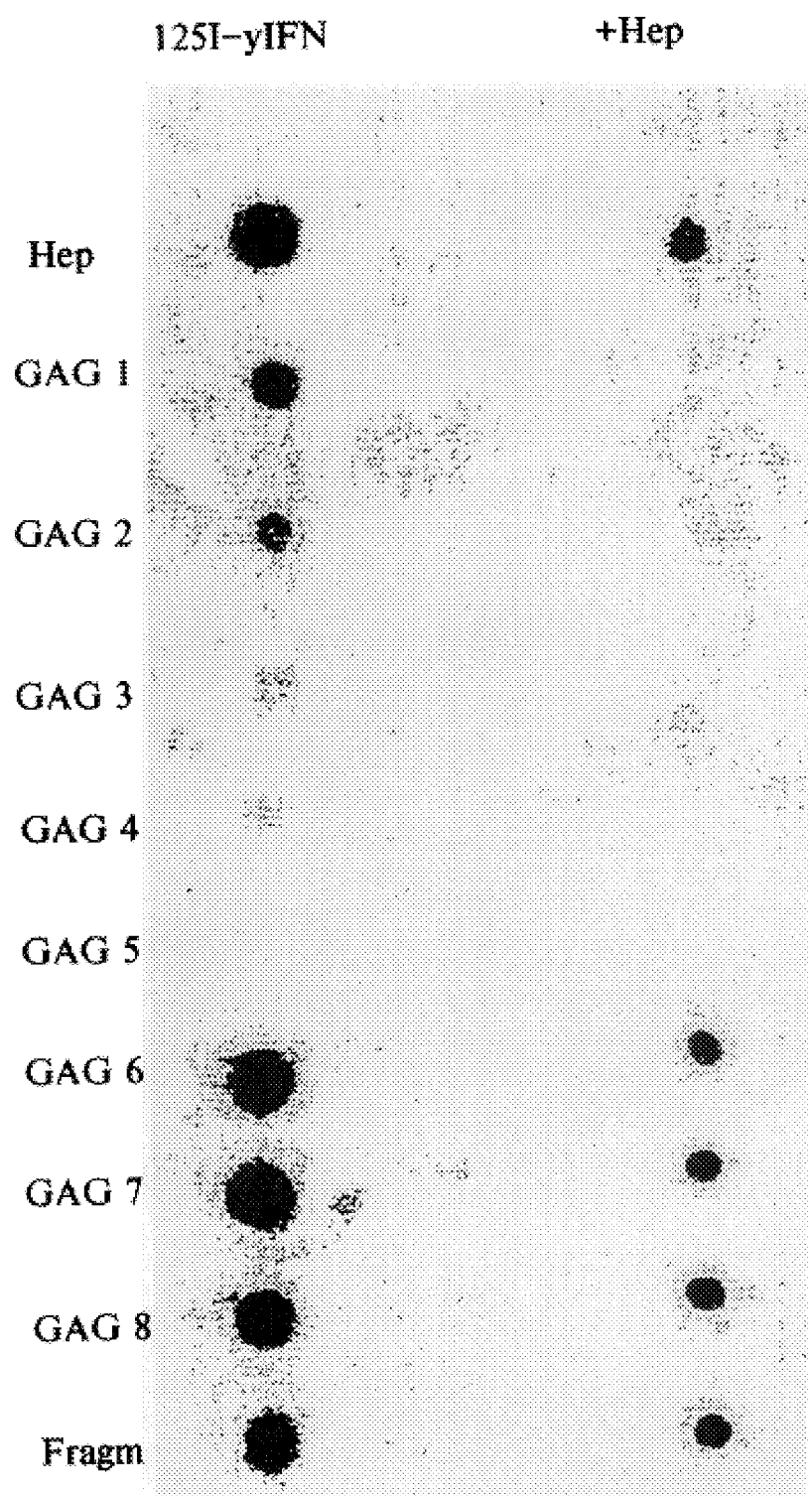
FIG. 8 shows the binding of $^{125}$I-IFN-γ to heparin, fragmin and various glycosaminoglycans.

Previously it has been demonstrated that IFN-γ can bind to cell-bound, HSPG or chondroitin sulfate proteoglycans (27,28). There is however unequivocal evidence whether this binding involves the interaction with the sulfate or carboxylic groups of the proteoglycan. We performed binding studies to address the question whether sulfation of GAG is required for IFN-γ binding. Our results demonstrated that heparin and supersulfated GAG can bind $^{125}$I-IFN-γ. However desulfated-N-acetylated GAG expressing only a low amount of sulfate (GAG 3–5) were not able to bind IFN-γ anymore. Desulfated-N-acetylated GAG with a higher amount of sulfate (GAG 1 and 2) were able to bin IFN-γ, although to a smaller extend than supersulfated GAG and heparin. The binding if $^{125}$I-IFN-γ to heparin or GAG on the nitrocellulose filter could be inhibited by coincubation of $^{125}$I-IFN- and a 3000 fold excess of fluidphase heparin. Under these conditions GAG 1 and 2 were not able to bind $^{125}$I-IFN-γ anymore whereas the binding to heparin, fragmin and supersulfated GAG was strongly reduced (FIG. 8).

TABLE 1

Characteristics of the various heparins and glycosaminoglycans used in this study

| Name | Sulfate [%] | Fxa [IU/mg] | FIIa [IU/mg] | $M_P$ | $M_r$ |
|---|---|---|---|---|---|
| Desulfated N-acetylated heparinoids | | | | | |
| GAC 1 | 7.3 | 0 | 0 | 3289 | 3802 |
| GAG 2 | 6.4 | 0 | 0 | 2992 | 3548 |
| GAG 3 | 5.5 | 0 | 0 | 2869 | 3382 |
| GAG 4 | 3.4 | 0 | 0 | 2364 | 2800 |
| GAG 5 | 1.2 | 0 | 0 | 1618 | 2074 |
| sulfated heparinoids | | | | | |
| GAG 6 | 14.2 | 26.1 | 39 | 7800 | 8360 |
| GAG 7 | 14.2 | 21.5 | 30 | 6000 | 7700 |
| GAG 8 | 13.7 | 25.8 | 28 | 5500 | 6300 |
| Commercially available heparins | | | | | |
| Braun | ND | ND | ND | 14000 | 18000 |
| Fragmin-P | ND | 160 | 70 | 4900 | 6000 |

*)Characteristics of the various heparins and glycosaminoglycans used in this study. $M_p$: total weight divided by number of molecules; $X_w$: molecular weights, ND, not done FIIa and Fxa activity was measured according to Handeland et al. (Assay of unfractionated and LMW heparin with chromogenic substrates: twin methods with factor Xa and thrombin, Thrombosis Res. 1984, 35: 627) with the first international standard for low molecuiar weight heparin (established in 1987, code no. 85/600).

Characteristics of the various heparins and glycosaminosglycans used in this study. $M_p$: total weight divided by number of molecules; $M_w$: molecular weights, ND, not done, FIIa and Fxa activity was measured according to Handeland et al. (Assay of unfractionated and LMW heparin with chromogenic substrates: twin methods with factor Xa and thrombin, Thrombosis Res. 1984, 35: 627) with the first international standard for low molecular weight heparin (established in 1987, code no. 85/600).

Dose-response of IFN-γ on MHC class I. class II and ICAM-1 expression on PTEC. The cells were stimulated for 72 hours using various concentrations of IFN-γ. Hereafter the expression of MHC class I ( . . . , left scale), Mhc class II ( . . . , right scale) and ICAM-1 ( . . . , left scale) was determined by FACS. The results expressed as mean fluorescence intensity of one representative experiment are show.

FIG. 2

Effect to heparin on MHC and ICAM-1 expression on IFN-γ stimulated HUVEC. IFN-γ stimulated (100 ng/ml for 72 hours) (gray bars) or unstimulated (white bars) HUVEC were incubated with various concentrations of heparin during the stimulation period. MHC and ICAM-1 expression were thereafter determined by FACS. The results expressed as mean fluorescence intensity of one representative experiment are show.

FIG. 3

Effect of heparin on MHC and ICAM-1 expression on IFN-γ stimulated PTEC. IFN-γ stimulated (10 ng/ml, for 72 hours) or unstimulated PTEC were incubated with various concentrations of heparin during the stimulation period. MHC and ICAM-7 expression of three replicate cultures were thereafter determined by FACS. A: MHC class I expression, B: MHC class II expression, C: ICAM-1 expression. The results are expressed as mean fluorescense intensity±2 SD.

FIG. 4

Effect of different heparins and glycosaminoglycans on MHC and ICAM-1 expression on IFN-γ stimulated HUVEC. IFN-γ stimulated (10 ng/ml, for 72 hours) (solid bars) or unstimulated (hatched bars) HUVEC were incubated with various heparins or glycosaminoglycans in a concentration of 3 mg/ml during the stimulation period. MHC and ICAM-1 expression of three replicate cultures were thereafter determined by FACS. A: MHC class I expression, B: MHC class II expression, C: ICAM-1 expression. The results are expressed as mean fluorescense intensity±2 SD.

FIG. 5

Effect of different heparins and glycosaminoglycans on MHC and ICAM-1 expression on IFN-γ stimulated (10 ng/ml, for 72 hours) (solid bars) or unstimulated (hatched bars) PTEC were incubated with various heparins or glycosaminoglycans in a concentration of 3 mg/ml during the stimulation period. MHC and ICAM-1 expression were thereafter determined by FACS. A: MHC class I expression, B: MHC class II expression, C: ICAM-1 expression. The results expressed as mean fluorescense intensity of one representative experiment are show.

FIG. 6

Comparison between GAG 6–8 and heparin for their ability to inhibit MHC and ICAM-1 expression on IFN-γ stimulated (10 ng/ml, for 72 hours) PTEC. PTEC were incubated with various concentrations of GAG 6 ( . . . ), GAG 7 ( . . . ), GAG 8 ( . . . ) or heparin ( . . . ) during the stimulation period. MHC and ICAM-1 expression of three replicate cultures were thereafter determined by FACS. The expression of these antigens in the absence of GAG (–GAG) or in the absence of IFN-γ (–IFN) was also determined. A: MHC class I expression, B: MHC class II expression, C: ICAm-1 expression. The results are expressed as mean fluorescense intensity±2 SD.

FIG. 7

Effect of $NaClO_3$ on the capacity of IFN-γ to stimulate MHC and ICAM-1 expression on PTEC. PTEC were treated one day prior to IFN-γ stimulation with 150 mM of $NaClO_3$ (solid bars) or 150 mM NaCl (hatched bars) as osmolarity control. Thereafter the cells were stimulated with various concentrations of IFN-γ for 72 hours in the presence of the same concentrations of $NaClO_3$ or NaCl. MHC and ICAM-1 expression of three replicate cultures were thereafter determined by FACS. A: MHC class I expression, B: MHC class II expression, C: ICAM-1 expression. The results are expressed as mean fluorescense intensity±2 SD. One star p<0.05; two stars p<0.01 by students t-test.

FIG. 8

Binding of $^{125}$I-IFN-γ to heparin, fragmin and various glycosaminoglycans. Heparin (Hep), glycosaminoglycan (GAG 1 to 8 and fragmin (Fragm) were bloted on a nitrocellulose filter as described in materials and methods. The strips were incubated with $^{125}$I-IFN-γ in the presence or absence of a 3000 fold excess of heparin.

We claim:

1. A pharmaceutical composition useful for protecting mammalian organs prior to and during a transplantation procedure, and which reduces the risk of organ rejection, which composition comprises
   (1) from 10 mg/L to 10,000 mg/L polysulfonated glycosaminoglycan having a sulfur content of at least 12.5% by weight which is effective at maintaining cell integrity and cell vitality, and which reduces the risk of organ rejection; and
   (2) from 5 to 100 g/L hydroxymethyl starch.

2. The composition of claim, 1, further comprising from 5 to 100 mmol raffinose.

3. The composition of claim 1, further comprising from 5 to 40 mmol $KH_2PO_4$, from 1 to 50 mmol $MgSO_4$, from 1 to 50 mmol adenosine, from 0.5 to 5 mmol allopurinol and from 1 to 10 mmol glutathionine.

4. The composition of claim 1, wherein the polysulfonated glycosaminoglycan has a sulfur content of from 13 to 16% by weight.

5. The composition of claim 1, wherein the polysulfonated glycosaminoglycan is in the form of a sodium, calcium or magnesium salt.

6. The composition of claim 1, wherein the polysulfonated glycosaminoglycan has an average molecular weight in the range of from 1,000 to 20,000 Dalton.

7. The composition of claim 1, wherein the polysulfonated glycosaminoglycan has an average molecular weight in the range of from 1,500 to 9,000 Dalton.

8. The composition of claim 1, wherein the polysulfonated glycosaminoglycan is in the form of a physiologically active salt or ester, or a mixture of a physiologically active salt and ester.

* * * * *